United States Patent [19]

Franco et al.

[11] Patent Number: 4,931,276
[45] Date of Patent: Jun. 5, 1990

[54] METHOD FOR INTRODUCING DESIRED AGENTS INTO RED BLOOD CELLS

[76] Inventors: Robert S. Franco, 1825 Sandcliff Dr., Cincinnati, Ohio 45230; Murray Weiner, 8915 Spooky Ridge La., Cincinnati, Ohio 45242

[21] Appl. No.: 323,499

[22] Filed: Mar. 13, 1989

Related U.S. Application Data

[63] Continuation-in-part of Ser. No. 115,241, Oct. 30, 1987, abandoned.

[51] Int. Cl.$^5$ ............................................. A61K 35/18
[52] U.S. Cl. ........................................ 424/533; 435/2
[58] Field of Search ............................ 424/101; 435/2

[56] References Cited

U.S. PATENT DOCUMENTS

| 4,224,313 | 9/1980 | Zimmermann et al. | 435/2 |
| 4,289,756 | 9/1981 | Zimmermann et al. | 435/2 |
| 4,478,824 | 10/1984 | Franco et al. | 424/101 |
| 4,652,449 | 3/1987 | Ropars et al. | 435/2 |

Primary Examiner—Sam Rosen
Attorney, Agent, or Firm—Frost & Jacobs

[57] ABSTRACT

A method of introducing effectively non-anionic agents into mammalian red blood cells without unacceptable loss of cell contents, utilizing an osmotic pulse technique wherein an aqueous diluent medium is provided containing the desired effectively non-anionic agent(s) and an effective amount of water-soluble polyanion. The polyanion is non-disruptive to the lipid outer membranes of red blood cells and contains at least two anionic moieties per molecule. The method comprises suspending packed red blood cells in an aqueous solution containing a compound which readily diffuses into and out of the cells, rapidly creating a trans-membrane osmotic gradient by diluting the solution containing the cells in suspension with an essentially isotonic aqueous medium containing an effective amount of polyanion and one or more effectively non-anionic agents to be introduced, thereby causing diffusion of water into the cells with consequent swelling and increase in permeability of the outer membranes, and maintaining the increase in permeability for a period of time sufficient only to permit transport of the desired agent and polyanion into the cells and diffusion of the compound out of the cells. In another embodiment, for use where a polyanion in the aqueous diluent medium would be undesirable, the red blood cells are subjected to shear stress immediately after the osmotic pulse occurs, resulting in resealing of the outer membranes of the cells and regaining their original size and shape, with the desired agent(s) incorporated therein.

9 Claims, 4 Drawing Sheets

A 10 sec.
B 20 sec.
C 30 sec.
D 60 sec.

METHOD FOR INTRODUCING DESIRED AGENTS INTO RED BLOOD CELLS

CROSS-REFERENCE TO RELATED APPLICATION

This application is a continuation-in-part of application Ser. No. 07/115,241, filed Oct. 30, 1987, now abandoned.

BACKGROUND OF THE INVENTION

This invention relates to the incorporation of a wide variety of therapeutically useful substances into mammalian red blood cells (RBC), which could not previously be accomplished without unacceptable losses of RBC contents and/or integrity. More particularly, the method of the present invention makes possible the introduction or incorporation of agents into RBC, such as peptides, purine and purine analogs, pyrimidine and analogs thereof, chemotherapeutic agents, antibiotic agents, and unnatural analogs of the nucleic acid bases adenine, guanine, cytosine and thymine. These and other water soluble substances, may be used for a desired slow continuous delivery or targeted delivery when the treated RBC carrier is later injected in vivo.

The method of this invention has particular utility when used in the so-called "osmotic pulse" mechanism taught in U.S. Pat. No. 4,478,824, issued Oct. 23, 1984, to the present applicants, the disclosure of which is incorporated by reference herein. The method of this patent involves incubating a packed RBC fraction in a solution containing a compound (such as dimethyl sulfoxide or glycerol) which readily diffuses into and out of cells, rapidly creating a trans-membrane osmotic gradient by diluting the suspension of RBC in the solution with a near-isotonic aqueous medium containing an anionic agent to be introduced (such as a phosphorylated inositol) which may be an allosteric effector of hemoglobin, thereby causing diffusion of water into the cells with consequent swelling thereof and increase in permeability of the outer membranes of the cells, and maintaining the increase in permeability for a period of time sufficient only to permit transport of the anionic agent into the cells and diffusion of the compound out of the cells.

However, the method of this patent is of limited effectiveness where the desired agent to be incorporated within the cells is not anionic or is anionic or polyanionic but is not present in the near-isotonic aqueous medium in sufficient concentration to cause the needed increase in cell permeability without cell destruction. The present invention constitutes a discovery that non-anionic agents can be introduced into RBC by addition to the near-isotonic aqueous medium of an effective amount of a water soluble polyanion, as hereinafter defined, which acts as a "co-factor" in causing the non-anionic agent or agents in the aqueous medium to be incorporated in the cells with optimum efficiency without unacceptable loss of cell contents. In effect, the polyanion co-factor provides a "free ride" for non-anionic agents through the outer membranes of the cells and into the cells during the relatively brief time period of increased permeability. This co-factor concept is also applicable for incorporation of anionic reagents whose introduction into RBC is desired in low concentrations not sufficient to provide the essential increase in permeability and transport into intact cells as described above. The term "effectively non-anionic" is thus used hereinafter to designate a desired agent to be introduced which is non-anionic, or which is anionic or polyanionic but is present in such low concentration in the near-isotonic aqueous medium as to be incapable of acting as a co-factor (i.e. less than the functional equivalent of 1 millimolar of inositol hexaphosphate, as explained below).

In a further embodiment, for use where the desired agent to be introduced would react with a polyanion co-factor to produce an insoluble product (or where use of a polyanion is otherwise undesirable), the present invention provides the application of shear induced resealing of RBC within a short period of time after the dilution step, in place of addition of a polyanion.

R. S. Franco et al. have disclosed part of the subject matter of the above-identified Pat. No. 4,478,824 in an article in *Life Science*, 32: 2763-2768 (1983).

R. E. Benesch et al., in *Biochemistry*, 16: 2594-1597 (1977) have shown that inositol hexaphosphate (IHP) binds to hemoglobin at the 2, 3 diphosphoglycerate site and causes a decrease in oxygen affinity. In addition to the osmotic pulse method for incorporating IHP into red cells disclosed in the above patent, a liposomal method is disclosed by Gerosonde in *Blut*, 39: 1-7 (1979), and a lysis-resealing method is disclosed by B. Teisseire et al. in Adv. Exp. Med., 180: 673-677 (1984).

P. C. Anderson et al., Biophys. J., 20: 181-191 (1977) describe two-phase release of hemoglobin for a hypotonic lysis. In the first phase the time to initial lysis is a function of the osmotic driving force and for hypotonic lysis is limited by the osmolarity of the cell interior.

M. P. Sheetz, in Semin. Hematol., 20: 175-188 (1983) showed that IHP at millimolar concentrations dissociates isolated red cell cytoskeletons and appears to act primarily on the spectrin-actin-band 4.1 complex. An earlier article by M. P. Sheetz et al., J. Biol. Chem., 255: 9955-9960 (1980) disclosed that exposure of intact membranes to a high concentration of polyphosphate did not result in elution of spectrin, from which it was inferred that this form of skeletal disruption does not interfere with binding to the bilayer membrane.

P. Heubsch et al., J. Cell. Physiol., 122: 266-272 (1985) showed that cytoskeletal detachment occurred in osmotically swollen cells and that with extreme changes in size the bilayer membrane is released from a deformational constraint which is present under normal conditions.

U.S. Pat. No. 4,224,313, issued Sept. 23, 1980, to U. Zimmermann et al. discloses a process for preparing a mass of loaded cells suspended in a solution by increasing the permeability of the cell membranes by osmotic pressure or an electric field, or both, incorporating loading material by passage from a solution through the membranes of increased permeability, restoring the original permeability by healing the membranes by regeneration effect, and separating the cells from the solution in which they were suspended. The loading material in solution includes a pharmaceutical substance having a capability of reacting chemically or physically with substances in solution outside the cell and which when incorporated in the cell would prematurely destroy the cell membranes, and at least one blood-compatible sugar and protein capable of providing hydrogen-bridge-bonding with the pharmaceutical substance or of entering into covalent bonds therewith, thereby inhibiting the reaction of the pharmaceutical substance with the cell membranes.

A description of experimental work leading to the present invention is contained in an article by R. S. Franco et al., J. Cell. Physiol., 129: 221-229 (1986).

Other publications by applicants include R. S. Franco et al., Am. J. Hematol., 17: 393-400 (1984) and R. S. Franco et al., Blood, 66 [suppl]: 277a (1984).

Other publications of which applicants are aware include U.S. Pat. No. 4,321,259, issued Mar. 23, 1982, to Y.-C. Nicolau et al.; Parsons et al. Chem. Abst., 91: 68355d (1979); Zimmermann et al. Chem. Abst., 94: 90235y (1981); Zimmermann et al. chem Abst., 89: 135585lm (1978); and Zimmermann et al. Chem. Abst., 86: 34228w (1977).

Despite the extensive work in the field of the present invention, as evidenced by the publications acknowledged above, there is still no method known in the prior art which provides introduction of non-anionic agents into RBC without unacceptable losses of RBC contents and without use of toxic or otherwise undesirable reagents and other materials in the process.

It is a primary objective of the present invention to provide a method which fulfills the above need.

SUMMARY OF THE INVENTION

The above object is achieved, in accordance with the invention, in a method of introducing desired agents into mammalian red blood cells without unacceptable loss of cell contents, comprising the steps of providing a supply of packed red blood cell; suspending and incubating the cells in a solution containing a compound which readily diffuses into and out of the cells, the concentration of the compound being sufficient to cause diffusion thereof into the cells so that the contents of the cells become hypertonic; rapidly creating a trans-membrane osmotic gradient by diluting the solution containing the hypertonic cells with an essentially isotonic aqueous medium in the presence of at least one desired agent to be introduced, whereby to cause diffusion of water into the cells with consequent swelling and increase in permeability of the outer membranes of the cells; and maintaining the increase in permeability of the membranes for a period of time sufficient only to permit transport of at least one agent into the cells and diffusion of the compound out of the cells; wherein the improvement comprises providing in the aqueous medium an effective amount of a water soluble polyanion which contains at least two anionic moieties per molecule and which is non-disruptive of the lipid outer membranes of red blood cells, and also providing at least one non-anionic agent or a low concentration of an anionic agent to effect transport of the at least one non-anionic agent or anionic agent into the cells.

As used hereinafter and in the appended claims, the term polyanion is intended to designate a compound which is water-soluble, non-disruptive to the lipid outer membranes of RBC and which contains at least two anionic moieties or functions per molecule.

In a further embodiment of the invention, where the use of a polyanion may be undesirable or impractical, the method comprises the steps of providing a supply of packed red blood cells; suspending and incubating the cells in an aqueous solution containing a compound which readily diffuses into and out of the cells, the concentration of the compound in the solution being sufficient to cause diffusion of the compound into the cells so that the contents of the cells become hypertonic; rapidly creating a trans-membrane osmotic gradient by diluting the solution containing the cells in suspension with an essentially isotonic aqueous medium containing at least one desired agent to be introduced, whereby to cause diffusion of water into the cells with consequent swelling and increase in permeability of the outer membranes thereof; maintaining the increase in permeability for a period of time sufficient only to permit transport of the desired agent into the cells and diffusion of the compound out of the cells; and immediately thereafter subjecting the cells to shear induced resealing.

DETAILED DESCRIPTION OF THE INVENTION

By way of background, human RBC have lipid bilayer outer membranes which are attached to proteinaceous cytoskeletons. The thickness of the bilayer outer membrane is about 100 Å. Although not intending to be bound by theory, it is believed that the use of a water-soluble polyanion in the method of the present invention results in partial dissociation of the proteinaceous cytoskeleton within a cell, thus enabling the cytoskeleton to expand with the lipid bilayer outer membrane (during the osmotic pulse) and to remain attached to the bilayer. Since the polyanion, which is non-disruptive to the lipid bilayer, needs to penetrate only the thickness of the bilayer outer membrane before coming into contact with the cytoskeleton and interacting therewith, the initial increase in permeability resulting from osmotic swelling and the effect of a polyanion on the cytoskeleton can occur in rapdi succession and almost simultaneously.

Figure 1:
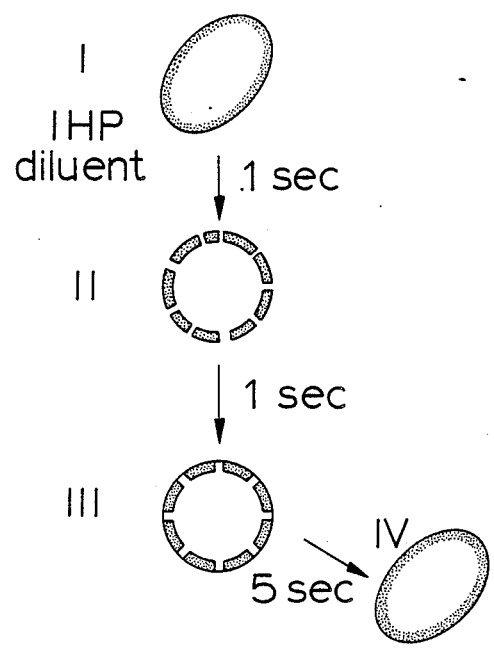
FIG. 1 is a schematic hypothetical mechanism for RBC changes with a polyanion present in the aqueous diluent medium.

Referring to FIG. 1, the theoretical mechanism for the behavior of cells during and immediately after an osmotic pulse is illustrated. A cell in intact form is shown at I surrounded by a diluent containing a polyanion such as IHP. After a time lapse of about 0.1 second during which the outer membrane expands in an osmotic pulse, the cytoskeleton becomes partially dissociated and expands with the outer membrane and remains attached to it as shown at II. The cell is then permeable for a short period of time of about one second, and some of the hemoglobin is lost. However, recovery is relatively rapid, and hemoglobin leakage stops after about one second. The cells remain mechanically fragile for several more seconds as shown at III. During this time it is believed that the cytoskeleton, which is still attached to the bilayer membrane, may regain its original state, e.g. after about 5 seconds, as shown at IV.

Effectively non-anionic agents which may advantageously be incorporated within RBC include peptides, purine analogs, pyrimidine analogs, chemotherapeutic agents and antibiotic agents. These agents frequently present drug delivery problems. Specific compounds include but are not limited to tryptophan, phenylalanine and other water-soluble amino acid compounds.

Several derivatives of the unnatural analogs of the nucleic acid bases adenine, guanine, cytosine and thymine are well known as useful therapeutic agents, e.g. 6 mercaptopurine (6 MP) and azathioprine which are commonly used as immunosuppressants and inhibitors of malignant cell growth; and azidothymidine (AZT) and analogs thereof which are useful as anti-viral agents, particularly in the treatment of AIDS. It has been shown that the action of these unnatural base deriatives is dependent on intra-cellular conversion thereof to phosphorylated forms. This is established in the following articles:

Chan, G. L. C. et al., "The Therapeutic Use of Azathioprine in Renal Transplantation" Pharmacotherapy 7(5): 165;14 177 (1987).

Mitsuya, H. et al., Proc. Natl. Acad. Sci. 83: 1911–1915 (March, 1986).

These publications indicate that the action of these unnatural base derivatives is a function of the amount and nature of the cells they enter, the capacity of such cells to convert the derivatives to a phosphorylated (i.e., active) form, and the potential of the cells involved to deliver their contents to other cells.

Prior to the present invention, it was usually not possible to use active phosphorylated moieties of the above derivatives as agents for treatment since such active moeities, even though they are polyanions after being phosphorylated, are administered in such low concentrations that they cannot penetrate RBC membranes. In this connection, it should be recognized that some of these derivatives must be used in low concentrations in order to avoid undesirable side effects. On the other hand, those phosphorylated derivatives which do not produce undesirable side effects, and which are not prohibitively expensive if used in higher concentrations, could act as a polyanion co-factor. Where low concentrations are needed, the method of the present invention makes it possible to incorporate phosphorylated moeities of unnatural analogs of nucleic acid bases into viable RBC and to deliver them to specific target cells at a uniform, continuous rate over a prolonged period of time after treatment. These phosphorylated agents can thus function both as polyanion co-factors and as effectively non-anionic agents. Non-limiting examples of such agents include phosphorylated 6 MP, phosphorylated azathioprine, phosphorylated AZT, phosphorylated dideoxycytosine and phosphorylated dideoxyadenosine.

Polyanions which are effective in the method of the invention include pyrophosphate, tripolyphosphate, phosphorylated inositols, 2, 3 diphosphoglycerate (2, 3 DPG), adenosine triphosphate, heparin, and polycarboxylic acids which are water-soluble, and non-disruptive to the lipid outer bilayer membranes of RBC.

Some, of not all, phosphate containing polyanions are allosteric effectors of hemoglobin. Sulfated compounds such as heparin are generally not allosteric effectors of hemoglobin. The effectiveness of polyanions as a co-factor in causing non-anionic agents to be incorporated in RBC has no direct relation to whether the polyanion is an allosteric effector of hemoglobin. The particular polyanion to be selected can be based on whether an allosteric effector of hemoglobin would be desirable for a particular treatment.

In conducting the osmotic pulse method of the present invention, the compound which readily diffuses into and out of the cells, in which the cells are initially suspended and incubated, may be dimethylsulfoxide, glycerol, or mixtures thereof. It has been found that the concentration of the compound in the aqueous solution is of some criticality in inducing an osmotic pulse. Thus, when using dimethylsulfoxide (DMSO) a concentration of 4% by weight proved to be ineffective in incorporating a desired agent and also resulted in no hemolysis. On the other hand, a concentration of 6% by weight DMSO did result in incorporation of a desired agent and a lysis of 20% to 40% at the dilution step. An upper limit of concentration is not critical but preferably should be maintained at about 10% by weight and is interdependent on the volume ratio of the diluent aqueous medium to the RBC and concentration of polyanion in the aqueous medium. The broad range is thus about 4.5% to 10%.

The concentration of polyanion in the diluent aqueous medium is not critical and may range broadly within the functional equivalent of an IHP concentration of 1 to 75 millimolar, and preferably from about 10 to about 60 millimolar. However, a concentration of less than 1 millimolar functional equivalent of IHP is ineffective in acting as a co-factor. Relatively high concentration of a polyanion causes RBC to reseal more rapidly, or in other words to provide a shorter osmotic pulse. As indicated above, the upper limit on concentration of polyanion is dependent also on the concentration of the compound in the initial aqueous solution, volume ratio of the diluent aqueous medium to the RBC and on the desired speed of the osmotic pulse.

As disclosed in the above-mentioned U.S. Pat. No. 4,478,824, the volume ratio of the diluent aqueous medium to the RBC in suspension ranges broadly from at least 1:3 to about 12:1 (preferably about 2:1 to 8:1), and the temperature of the diluent medium should range from about 20° to 30° C.

While not critical, the aqueous solution and diluent medium are preferably adjusted to physiologic pH.

It will be recognized that when the osmotic pulse is completed and the cells reseal as indicated at IV in FIG. 1, a portion of the polyanion is trapped within the cell. Where the polyanion is an allosteric effector of hemoglobin, it is believed that the polyanion transfers from the cytoskeleton to the hemoglobin, thus expediting the return of the disrupted cytoskeleton to its original state. Where the polyanion is not an allosteric effector of hemoglobin, the presence of polyanion trapped within the cell after the osmotic pulse is completed does not prevent the cytoskeleton from regaining its original state since the amount of polyanion within the cell is relatively small (in comparison to the concentration of polyanion in the diluent medium) and since the polyanion is further diluted by other contents within the cell after the osmotic pulse is completed. The polyanion may also be selected from agents which are normally components of the cell and enter into normal metabolic processes of the cell (e.g. pyrophosphate).

Figure 2:
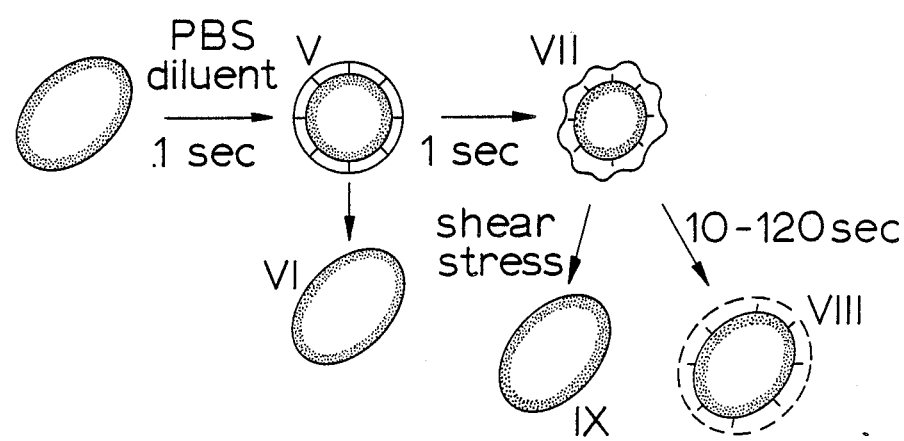
FIG. 2 is a schematic hypothetical mechanism for RBC changes with a phosphate buffered saline diluent medium.
Figure 3:
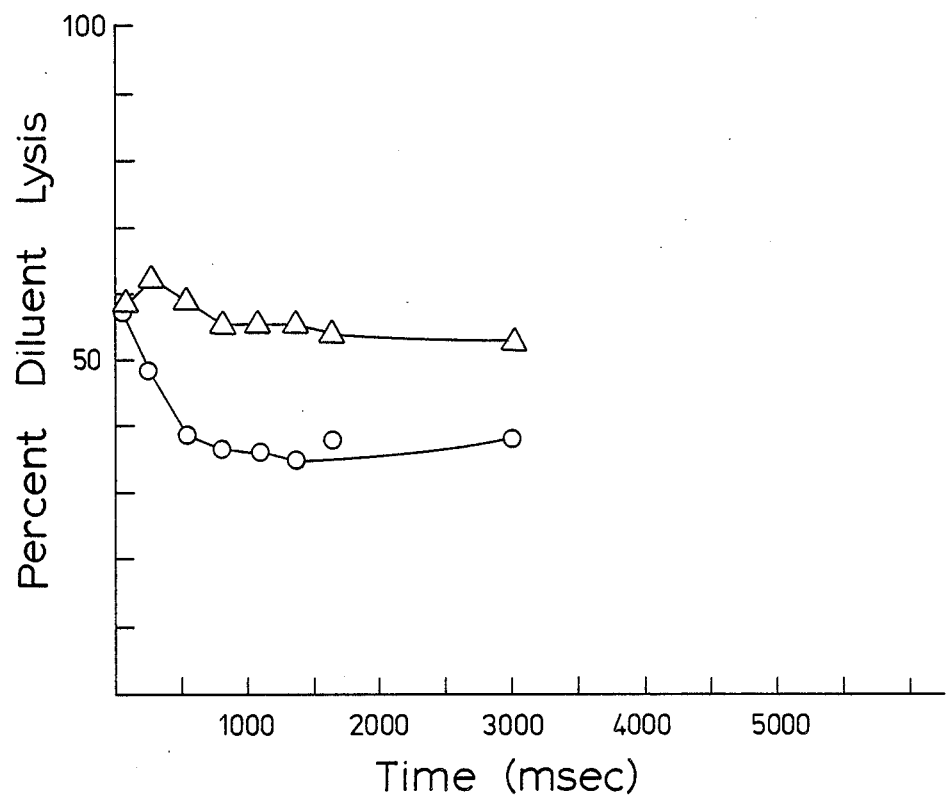
FIG. 3 is a graphic illustration of the percent of lysis for a diluent containing phosphate buffered saline, both with and without shear induced resealing.

Reference is next made to FIG. 2 which illustrates the hypothetical mechanism involved in the embodiment of the invention wherein a polyanion is not added to the aqueous diluent medium in situations where the presence of a polyanion may be undesirable. The intact cell is illustrated at I, in an aqueous diluent which may contain, e.g. phosphate buffered saline (PBS). PBS is neither an agent nor a co-factor, but is added in order to provide an essentially isotonic aqueous medium. As in the first embodiment, an osmotic pulse occurs relatively rapidly within about 0.1 second. The outer lipid bilayer membrane swells as shown at V. Since there is no polyanion present to dissociate the cytoskeleton, it apparently remains intact and regains its original state as shown at VI relatively rapidly, if the amount of osmotic stress is not excessive. On the other hand, where the osmotic stress, as determined by the concentration of the compound (e.g. DMSO) in the initial solution is high, some cells appear to go through a transitional form for several seconds, as shown at VII, lose substantially all hemoglobin and become "ghosts" as indicated VIII. It is believed that the difference between groups of cells which regain their original state as indicated at VI and those which go to the transitional form illustrated at VII is whether or not the cytoskeletons remain attached to the bilayer outer membranes. However, where the group of cells in the transitional form VII are subjected to shear stress at an appropriate time, surprisingly the cells undergo resealing and regain substantially their original state as indicated at IX. This has been confirmed experimentally by means of a capillary-induced shear stress, as described in greaer detail hereinafter. Referring to FIG. 3, it will be apparent that at 60 msec there is little difference in percent lysis between the capillary-induced shear test and the control (no capillary). At increasing times, there is progressively less lysis with the capillary-induced shear stress up to about 750 msec, after which the difference between the capillary-induced shear and control points remains constant for at least 2 seconds, and thereafter may tend to decrease. When the capillary-induced stress is applied about one second after dilution, the healing effect on the cells is quite marked, as shown in FIG. 3.

The shear stress was applied by passing RBC, following the osmotic pulse, through a glass capillary tube of 2×0.1 cm immediately after the selected delay time. The collected cell suspension was then centrifuged for 5 minutes at 1000 g, and the supernatant was removed and saved. The packed cells were incubated for 30 minutes at 37° C. to promote healing. After incubation, the cells were washed with PBS, and samples were taken for measurement of recovered hemoglobin. The percent lysis were calculted from the recovered hemoglobin and the hemoglobin lost at the dilution and wash steps. Control runs were performed in which the conditions were identical except that passage through the capillary was eliminated.

The possibility of effect of the capillary on the flow rates of the pumps of the osmotic pulse itself by inducing a higher backpressure was eliminated in additional control experiments by delivering the diluted cells into a pressurized receiving vessel.

Figure 4:
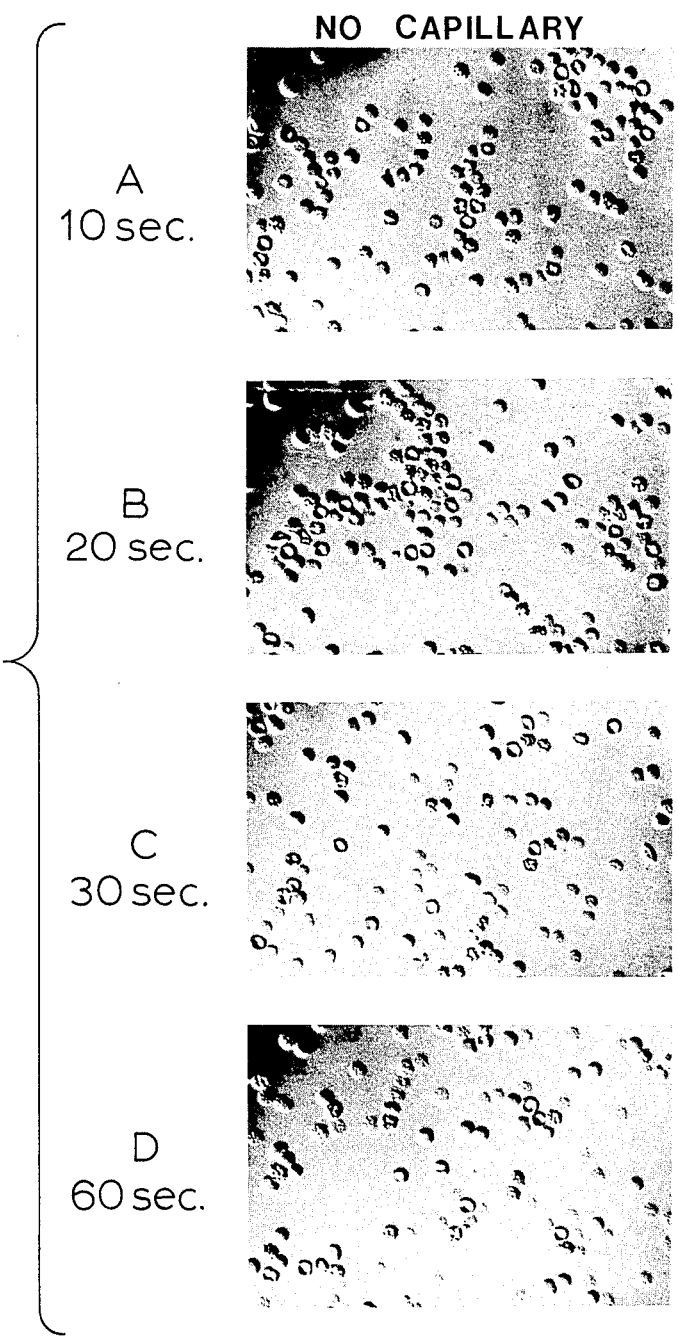
FIGS. 4A through 4D are photomicrographs (500×magnification) of RBC with a phosphate buffered saline diluent medium and without shear induced resealing.
Figure 5:
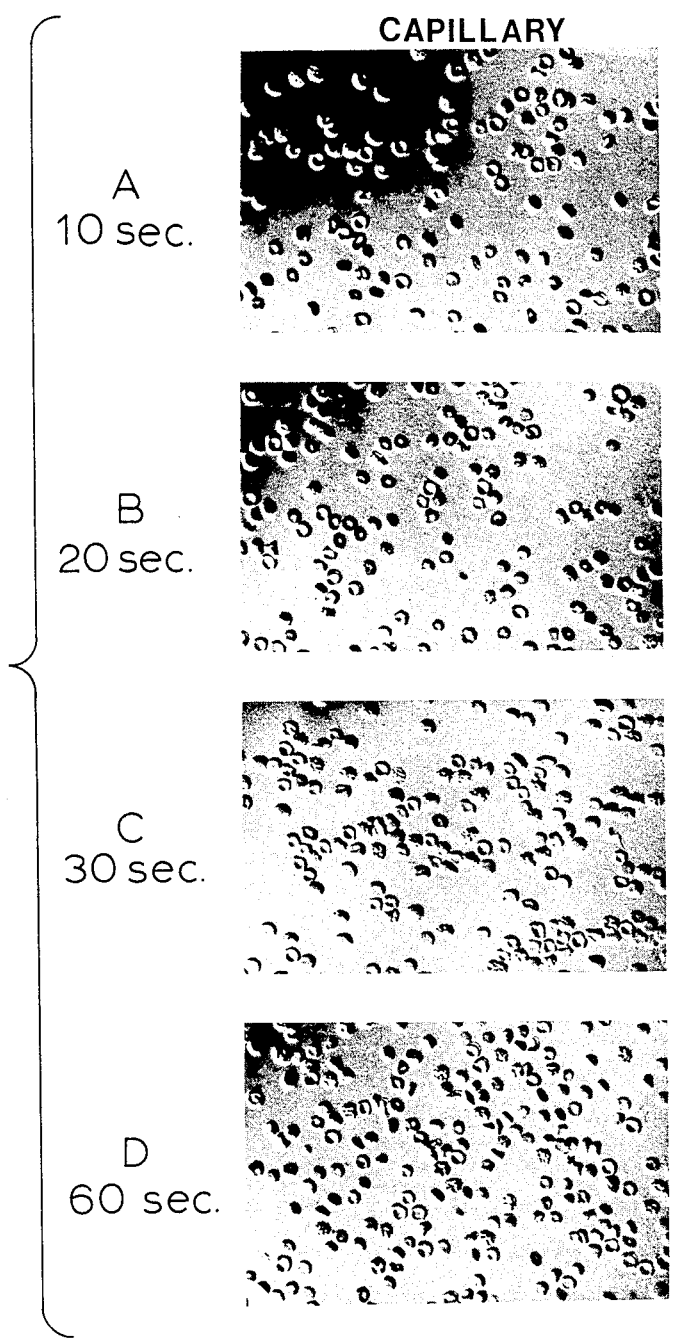
FIGS. 5A through 5D are photomicrographs (500×magnification) of RBC with phosphate buffered saline diluent medium after shear induced resealing.

In other experiments, cells were fixed by mixture with formalin fixative solution. Preparations of fixed cells were then observed and photographed under Normarski optics at 500×magnificaton. FIGS. 4 and 5 are photomicrographs of these fixed cells diluted with PBS at various delay times ranging from 10 seconds to 60 seconds. FIGS. 4A through 4D show the appearance of the control cells while FIGS. 5A through 5D show the appearance of cells subjected to capillary-induced shear stress. It will be apparent that the control cells which were not subjected to shear stress exhibited a gradual second-phase lysis between 10 and 20 seconds with resulting cellular morphology of ghosts and intact cells. On the other hand, cells subjected to capillary stress at 1.5 seconds after dilution demonstrated no further loss of hemoglobin between 10 and 60 seconds and a much more homogeneous cell population.

It was found that the concentration of DMSO in the initial solution had a pronounced effect on hemolysis in this embodiment. A concentration of 5.15% DMSO was optimum. Small decreases resulted in no lysis (and no osmotic pulse), while relatively small increases resulted in complete lysis of the cells. A range of about 4.5% to 7% may be used.

Aromatic amino acids and small peptides prepared from them can increase the solubility of S hemoglobins, according to C. Noguchi et al., *Biochemistry*, 19, 5455-5459 (1978). Of the amino acids tested tryptophan has about twice the effectiveness on a molar basis of phenylalanine. Tryptophan is transported through the RBC membrane by means of a different and much slower pathway than phenylalanine but is still too permeable for lasting effect. However, many effective peptides prepared from aromatic amino acids are not permeable and may have utility if they are efficiently introduced into RBC. In the following specific example, tryptophan (which is not polyanionic) was selected as a model compound, and pyrophosphate was selected as the polyanion:

EXAMPLE 1

Blood was obtained from normal human volunteers with informed consent, anticoagulated with CPD, and used the same day. The red cells were washed once with PBSW and the buffy coat removed. One volume of an aqueous solution containing 18% (three times the desired final concentration) of DMSO was added slowly to two volumes of packed RBC to give a hematocrit of about 50%. A syringe containing this RBC suspension was placed in a first syringe pump set to deliver 25 ml/min.

A diluent medium was prepared by dissolving 60.0 g pyrophosphate, tetrasodium salt (Sigma P-9146) in 1 liter of distilled water and adjusting the pH to 7.2 with HCl. This solution was then diluted with distilled water to obtain 292-302 mOs/kg, and 1% w/v polyethylene glycol, average molecular weight 3,350 (Sigma P-3640), was added to give 305-315 mOs/Kg. Either 5 mM or 50 mM of tritium-labelled tryptophan were added to the diluent medium. The osmolality with the higher concentration of tryptophan was 329 mOs/kg.

A second syringe of the pyrophosphate-tryptophan diluent medium was placed in a second syringe pump set to deliver 85 ml/min. The outflows from the first and second pumps were mixed in a simple chamber comprising a 3-way disposal valve (in which the osmotic pulse was initiated) and collected in a receiving vessel. All the above steps were conducted at room temperature.

The cell suspension was next centrifuged (5 mins at 1000×g), the supernatant was removed, and the packed cells were incubated for 30 minutes at 37° C. After incubation, the cells were washed once with 37° C. PBS and twice with room temperature PBS. Hemoglobin recovery was 82% for the 50 mM tryptophan diluent concentration, calculated from the hemoglobin in the recovered cells and the hemoglobin lost during the dilution and wash steps.

Control tests were also run under identical conditions except that no DMSO was added to the RBC suspension. The incorporation of tryptophan into RBC by the control test and by the method of the present invention is summarized in Table I. In this Table, intra-cellular tryptophan concentration was measured immediately after treatment (t=0) and after incubation in a tryptophan-free medium for two hours (t=2). It is evident that a very high concentration of tryptophan is introduced into RBC in a very short period of time by the method of this invention.

TABLE I

| Test No. | Sample Type | Diluent TRP, mM | Intra-cell. TRP, mM t = 0 | Intra-cell. TRP, mM t = 2 hr |
|---|---|---|---|---|
| 1 | control | 5 | 0.33 | 0.16 |
| 1 | present invention | 5 | 1.10 | 0.71 |
| 2 | control | 5 | 0.28 | 0.08 |
| 2 | present invention | 5 | 1.17 | 0.69 |
| 3 | control | 50 | 3.65 | N.D.* |
| 3 | present invention | 50 | 13.08 | N.D.* |

*N.D. = Not determined

We claim:

1. In a method of introducing desired agents into mammalian red blood cells without unacceptable loss of cell contents, comprising the steps of:
   providing a supply of packed red blood cells;
   suspending and incubating said cells in a solution containing a compound which readily diffuses into and out of said cells, the concentration of said compound being sufficient to cause diffusion thereof into said cells so that the contents of said cells become hypertonic;
   rapidly creating a trans-membrane osmotic gradient by diluting said solution containing said hypertonic cells with an essentially isotonic aqueous medium in the presence of at least one desired agent to be introduced, whereby to cause diffusion of water into said cells with consequent swelling and increase in permeability of the outer membranes of said cells; and
   maintaining said increase in permeability of said membranes for a period of time sufficient only to permit transport of said at least one agent into said cells and diffusion of said compound out of said cells;
   the improvement which comprises providing in said aqueous medium an effective amount of a water soluble polyanion which contains at least two anionic moeities per molecule and which is non-disruptive of the lipid outer membranes of red blood cells, and also providing at least one non-anionic agent or a low concentration of an anionic agent to effect transport of said at least one non-anionic agent or anionic agent into said cells.

2. The method of claim 1, wherein said compound is dimethyl sulfoxide, glycerol, or mixtures thereof.

3. The method of claim 1, wherein said polyanion is selected from the group consisting of pyrophosphate, tripolyphosphate, phosphorylated inositols, adenosine triphosphate, 2, 3 diphosphoglycerate, heparin, polycarboxylic acids, phosphorylated analogs of the nucleic acid bases adenine, guanine, cytosine and thymine, and mixtures thereof.

4. The method of claim 3, wherein said polyanion is an allosteric effector of hemoglobin.

5. The method of claim 3, wherein said polyanion is not an allosteric effector of hemoglobin.

6. The method of claim 1, including the step of separating and washing said cells to obtain a sterile fraction of substantially intact cells containing intra-cellular desired agent.

7. The method of claim 1, wherein said desired agent is selected from the group consisting of peptides, chemotherapeutic agents, antibiotic agents, tryptophan, phenylalanine, phosphorylated 6 mercaptopurine, phosphorylated azathioprine, phosphorylated azidothymidine, phosphorylated dideoxycytosine, phosphorylated dideoxyadenosine, derivatives thereof, and mixtures thereof.

8. The method of claim 2, wherein the concentration of said compound in said aqueous solution ranges from about 4.5% to 10% by weight.

9. The method of claim 1, wherein the concentration of said polyanion in said aqueous medium is the functional equivalent of from about 1 to about 75 millimoles of inositol hexaphosphate.

* * * * *